(12) United States Patent
Niimi et al.

(10) Patent No.: US 7,241,861 B2
(45) Date of Patent: Jul. 10, 2007

(54) HIGH DENSITY LIPOPROTEIN-REACTIVE PEPTIDES

(75) Inventors: Manabu Niimi, Gunma (JP); Kazushi Kanatani, Gunma (JP); Masakazu Adachi, Gunma (JP)

(73) Assignee: Japan Immunoresearch Laboratories Co., Ltd., Takasaki-shi (JP)

( * ) Notice: Subject to any disclaimer, the term of this patent is extended or adjusted under 35 U.S.C. 154(b) by 317 days.

(21) Appl. No.: 10/476,872

(22) PCT Filed: May 15, 2002

(86) PCT No.: PCT/JP02/04697

§ 371 (c)(1), (2), (4) Date: Nov. 12, 2003

(87) PCT Pub. No.: WO02/092630

PCT Pub. Date: Nov. 21, 2002

(65) Prior Publication Data

US 2004/0242474 A1    Dec. 2, 2004

(30) Foreign Application Priority Data

May 15, 2001    (JP)    ............................. 2001-144304

(51) Int. Cl.
*C07K 14/775* (2006.01)
*C07K 14/47* (2006.01)
*A61K 38/17* (2006.01)

(52) U.S. Cl. ......................................... 530/324; 514/12

(58) Field of Classification Search .................... None
See application file for complete search history.

(56) References Cited

U.S. PATENT DOCUMENTS 6,635,623 B1 * 10/2003 Hoogeveen et al. ........... 514/44

FOREIGN PATENT DOCUMENTS

| JP | 63-243878 | 10/1988 |
|---|---|---|
| JP | 6-138122 | 5/1994 |
| WO | 87/02062 | 4/1987 |
| WO | 97/43311 | 11/1997 |
| WO | 98/56938 | 12/1998 |

OTHER PUBLICATIONS

NCBI Protein Database Accession No. P04114 (Nov. 1, 1986).*
Ylitalo et al. 1999. Life Sciences. 64(21): 1955-1965.*
Moghadasian, 2002. Life Sciences. 70: 855-865.*
Maxfield et al, 2005, Nature. 438(7068): 612-621.*
Knott et al, 1986. Nucleic Acids Research, 14(18): 7501-7503.*
Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Frei et al, 1992 (Journal of Cell Biology, 118(1): 177-194).*
Dhople et al (2005, Peptides, 26: 217-225).*
Guerrini et al (2000, Peptides, 21: 923-933).*
Medical Practice, vol. 18, No. 3, pp. 473-480, With Partial English Translation 2001, Authors: Sakai and Yamasita.
Domyakukoka, vol. 20, No. 2-3, pp. 79-88, With English Summary, 1992, Authors: Nakajima et al.
Katsuyuki Nakajima, et al., "Cholesterol in remnant-like lipoproteins in human serum using monoclonal anti apo B-100 and anti apo A-I immunoaffinity mixed gels", Clinica Chimica Acta 223, pp. 53-71 1993.
David W. Garber, et al., "A new synthetic class A amphipathic peptide analogue protects mice from diet-induced atherosclerosis", Journal of Lipid Research, vol. 42, No. 4, XP-002314523, Apr. 2001, pp. 545-552.
Odette S. Reyes, et al., "Immunization With a Novel Human Apo B100 Related Peptide Reduces Atherosclerosis and Inflammation in Apo E Null Mice", Journal of the American College of Cardiology, vol. 39, No. 5, XP-009042981, Mar. 6, 2002, p. 240A.

* cited by examiner

*Primary Examiner*—Elizabeth Kemmerer
*Assistant Examiner*—Zachary C. Howard
(74) *Attorney, Agent, or Firm*—Oblon, Spivak, McClelland, Maier & Neustadt, P.C.

(57) ABSTRACT

A high-density lipoprotein-reactive peptide or a foam cell-reactive peptide as set forth in the following (a) or (b): (a) a peptide comprising the amino acid sequence represented by SEQ ID NO: 1; and (b) a peptide comprising an amino acid sequence derived from the amino acid sequence as specified in the above (a) by substitution, deletion, addition, or insertion of one or more amino acid residues and being capable of specifically binding to high-density lipoprotein cholesterol or withdrawing cholesterol from foam cells. Thus, peptides having novel amino acid sequences and being capable of specifically binding to HDL cholesterol or withdrawing cholesterol from foam cells are provided. These peptides are useful as drugs for various diseases caused by arteriosclerosis, lipid metabolic errors, and peripheral cholesterosis.

17 Claims, 5 Drawing Sheets

HIGH DENSITY LIPOPROTEIN-REACTIVE PEPTIDES

TECHNICAL FIELD

The present invention relates to a peptide capable of specifically binding to high-density lipoprotein (HDL) cholesterol, to a foam-cell-reactive peptide, and to drugs containing such peptides.

BACKGROUND ART

In blood, lipids are always present as lipoproteins. The mechanisms of transport and metabolism of lipids by the mediation of lipoproteins are now being clarified.

Triglycerides (TGs), cholesterols, and cholesteryl esters (CEs) are secreted in the form of very low density lipoproteins (VLDLs) into blood. VLDLs act to provide peripheral tissue with a portion of TGs in the form of fatty acids, and also participate in transfer and exchange of a portion of lipids between HDLs and intermediate lipoproteins (IDLs). IDLs, which undergo lipid exchange with HDLs, lose TGs, to thereby become low density lipoproteins (LDLs), which in turn are taken into peripheral tissue and supply cholesterols.

Meanwhile, cholesterols which have become useless in the peripheral tissue are withdrawn by HDLs and converted into CEs, and subsequently exchanged with TG contained in the above-mentioned TG-rich VLDLs, IDLs, or LDLs, until they are reversely transported to the liver. This process of transferring cholesterols from the peripheral tissue such as blood walls to the liver is known as reverse cholesterol transport (RCT), and this process is considered to contribute to prevention of excessive build-up of cholesterols (Medical Practice, vol. 18, No. 3, 473-480 (2001)).

Substances that are known to play an important role in the reverse cholesterol transport or lipid exchange between HDLs and TG-rich lipoproteins include enzymes such as lecithin cholesteryl acyltransferase (LCAT), hepatic lipase (HTLC), lipoprotein lipase (LPL), and cholesteryl ester transport proteins (CETP). However, their action mechanisms, interactions between lipoproteins, and relation with lipid metabolic errors have not yet been elucidated.

Foam cells take part in cholesterol build-up in the peripheral tissue. That is, macrophages derived from monocytes in blood and present in the walls of blood vessels gobble up fat and accumulate large amounts of fat particles (primarily CEs) therein. Chemically modified LDLs are taken into the macrophage cells endlessly by the mediation of scavenger receptors, whereby foam cells are formed. Emerging of foam cells is known to be a factor critical to the onset and development of arteriosclerosis in high cholestrolemia.

An object of the present invention is to provide novel information useful for elucidating interactions between HDL and TG-rich lipoproteins.

The present invention also provides information about a specific component of TG-rich lipoproteins which participate in the above interactions, regions of such component, and structures, and further provides an HDL-reactive peptide having a specific structure.

The present invention also provides novel information about interactions between cholesterols built up in peripheral tissue such as blood vessel walls and lipoproteins, and in particular information concerning cholesterol efflux mechanism.

Moreover, the present invention provides means useful for the evaluation and amelioration of lipid metabolic errors which greatly affect the onset, development, prognosis, etc. of heart diseases such as myocardial infarction as well as different types of arteriosclerosis, including cerebrovascular disorders such as cerebral apoplexy.

DISCLOSURE OF THE INVENTION

The present inventors performed studies on lipid metabolic errors, and provided, among others, a remnant-like lipoprotein (RLP) serving as a clinical index which indicates such errors (see, for example, Arteriosclerosis, 20, 79-88 (1992); Clin. Chim. Acta., 223, 53-71 (1993); or Japanese Patent No. 2657225) and a technique for improvement or measurement of CETP participating in the above-described lipid exchange (Japanese Patent No. 3043528).

During pursuit of their subsequent studies, the present inventors have quite unexpectedly obtained a novel finding that HDL reacts directly with LDL. The present invention has been accomplished on the basis of a determination that this reaction proceeds by the mediation of a specific region of apo B-100 of LDL.

The novel finding that HDL reacts directly with a TG-rich lipoprotein to thereby exchange lipids satisfactorily explains RLP's characteristics and the causes of the above-described phenomena of RLP, which is an abnormal lipoprotein believed to be slowly metabolized and built up in blood. RLP is a serum lipoprotein whose characteristic is that RLP does not react with an antibody for apo B-100 (a structural apoprotein of VLDL, IDL, and LDL) or for apo A-I (a structural apoprotein of HDL). Thus, different from normal TG-rich lipoproteins, RLP is believed not to provide the specific region of apo B-100, which participates in the reaction with HDL, and therefore RLP cannot react with HDL, leading to stagnation in lipid exchange and metabolism of RLP.

Accordingly, the present invention contemplates provision of novel information that HDL reacts directly with TG-rich VLDL, IDL, and LDL by the mediation of apo B-100 contained in the VLDL, IDL, and LDL in the above-described lipid transport mechanism or in the lipoprotein metabolism mechanism. Moreover, the present invention contemplates provision of a specific region determined to participate in the reaction of apo B-100.

Thus, the present invention provides an HDL-reactive peptide of the following (a) or (b):
(a) a peptide having the amino acid sequence represented by SEQ ID NO: 1; or
(b) a peptide having an amino acid sequence represented by (a) with one or more amino acid residues having being modified through substitution, deletion, addition, or insertion, and having a specific binding ability to HDL cholesterol.

The present inventors have further performed a variety of studies on effect of the peptide and the modified peptide, and have found that these peptides have an effect of cholesterol efflux from foam cells produced in the early stage of arteriosclerosis. A substance having the effect of cholesterol efflux from foam cells prevents plaque formation, thrombosis formation, development of arteriosclerosis from the foam cells, or similar reactions. Therefore, the peptide and the modified peptide are useful as a drug for improving lipid metabolic errors or a drug for preventing or treating arteriosclerosis.

The present invention provides a foam-cell-reactive peptide of the following (a) or (b):
(a) a peptide having the amino acid sequence represented by SEQ ID NO: 1; or (b) a peptide having an amino acid sequence represented by (a) with one or more amino acid residues having being modified through substitution, deletion, addition, or insertion, and inducing cholesterol efflux from foam cells.

The present invention also provides a drug such as a peripheral-tissue-cholesterol efflux drug, a drug for improving lipid metabolic errors, or a drug for preventing or treating arteriosclerosis, containing the HDL-reactive peptide or the foam-cell reactive peptide as an active ingredient.

The present invention also provides a drug composition such as a peripheral-tissue-cholesterol efflux drug, a drug for improving lipid metabolic errors, or a drug for preventing or treating arteriosclerosis, containing the HDL-reactive peptide or the foam-cell-reactive peptide, and a pharmacologically acceptable carrier.

The present invention also provides use of the HDL-reactive peptide or the foam-cell-reactive peptide in production of a drug such as a peripheral-tissue-cholesterol efflux drug, a drug for improving lipid metabolic errors, or a drug for preventing or treating arteriosclerosis.

The present invention also provides a method for treating cholesterol build-up in peripheral tissues, lipid metabolic errors, or arteriosclerosis, comprising administering, to a subject in need thereof, the HDL-reactive peptide or the foam-cell-reactive peptide in an effective amount.

In the present specification, abbreviations used to designate amino acids, peptides, nucleotide sequences, nucleic acids, etc. accord with the regulations of IUPAC or IUB, "Guideline for Preparing a Specification Containing a Nucleotide Sequence or an Amino Acid Sequence" (edited by the Japanese Patent Office), or customary codes employed in the art.

Amino acid sequences and site numbers of apo B-100 are designated in accordance with "apolipoprotein B-100 precursor-human, ACCESSION: LPHUB, PID: g71789, NCBI Sequence Viewer."

BEST MODE FOR CARRYING OUT THE INVENTION

Figure 1:
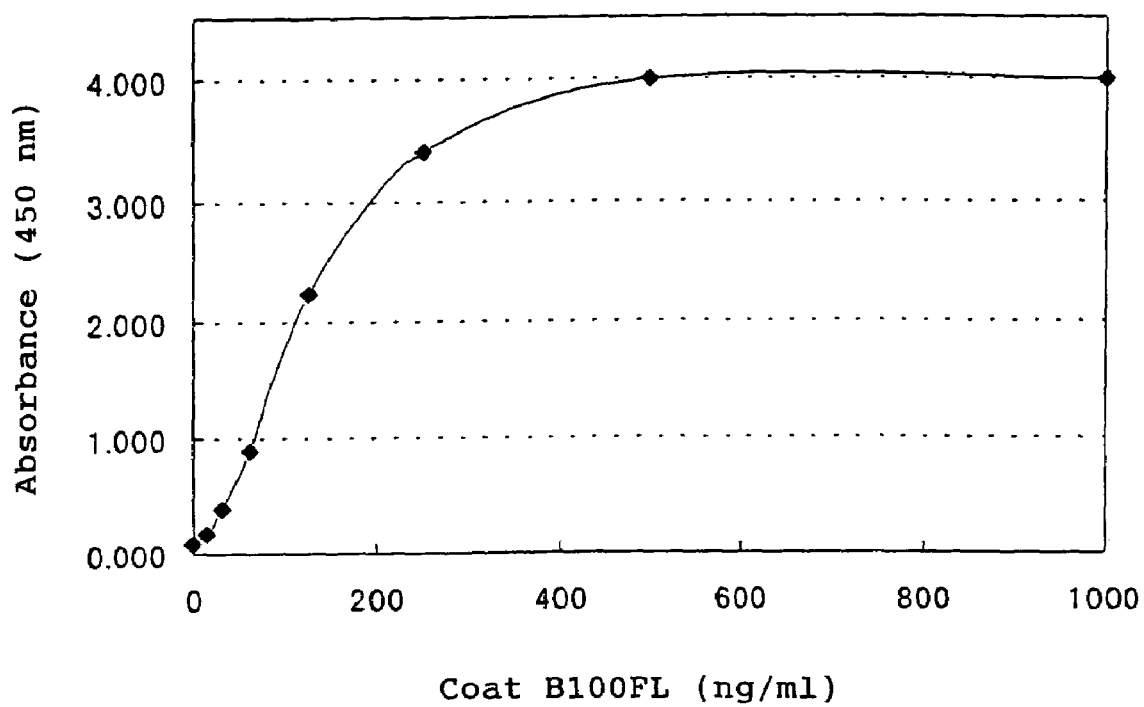
FIG. 1 shows reactivity of B100FL with anti-apo B-100 monoclonal antibody (JI-H)

The HDL-reactive polypeptide of the present invention will be described in detail.

A characteristic feature of the HDL-reactive peptide of the present invention resides in its specific binding ability to HDL cholesterol.

As used herein, the expression "has a specific binding ability to HDL cholesterol" refers to a situation in which the HDL-reactive peptide exhibits affinity specifically with free cholesterol and/or CE contained in HDL to thereby bind specifically thereto. The expression also refers to a situation in which free cholesterol and/or CE contained in HDL exhibit affinity specifically with the HDL-reactive peptide to thereby bind specifically thereto.

SEQ ID NO: 1 is an amino acid sequence of a characteristic peptide exhibiting binding ability to HDL cholesterol. That is, peptides having such an amino acid sequence have a specific binding ability to HDL cholesterol. Accordingly, such peptides are preferred embodiments of the HDL-reactive peptide of the present invention.

SEQ ID NO: 1 represents a region contained in apo B-100 (a structural protein of VLDL, IDL, and LDL) and having 51 amino acid residues; i.e., the 2,297th to the 2,347th amino acid residues of apo B-100.

Interestingly, the region represented by SEQ ID NO: 1 contains a region which is considered to be an epitope for the monoclonal antibody "JI-H" (an apo B-100 antibody used in measurement of RLP) (J. Clin. Ligand Assay, 19 (3), 177 (1996)). Therefore, the finding in the present invention well agrees with the fact that RLP, an abnormal TG-rich lipoprotein which is slowly metabolized and is built up in blood, does not have binding ability to the monoclonal antibody.

In relation to the HDL-reactive peptide, the amino acid sequence of SEQ ID NO: 1 may take a modified form in which partial amino acids, or one or more amino acid residues of the sequence, have been modified, so long as the peptide exhibits binding ability to HDL cholesterol.

No limitations are imposed on the degree and the site of the modification (i.e., substitution, deletion, addition, or insertion), so long as a peptide having the modified amino acid sequence exhibits the same effect as peptides having the amino acid sequence of SEQ ID NO: 1; i.e., the peptide has binding ability to HDL cholesterol. Examples of the mutant include peptides having about 100 amino acid residues, and the mutant preferably has about 6 to about 60 amino acid residues, more preferably about 20 to about 50 amino acid residues. An essential requirement is that the mutant have the six amino acid residues represented by SEQ ID NO: 4, and preferably the mutant has the 20 amino acid residues represented by SEQ ID NO: 5. Examples of the mutant include a peptide having the 30 amino acid residues represented by SEQ ID NO: 2, and a peptide having the 30 amino acid residues represented by SEQ ID NO: 3. The HDL-reactive peptide of the present invention is particularly preferably a peptide having the amino acid sequence of SEQ ID NO: 1.

Whether or not the HDL-reactive peptide has binding ability to HDL cholesterol can be confirmed through a test in accordance with a customary method. A specific example of the test will be described below in Examples.

The foam-cell-reactive peptide of the present invention will be described in detail. A characteristic feature of the foam-cell-reactive peptide resides in its effect of effluxing cholesterol from foam cells.

In relation to the foam-cell-reactive peptide, the amino acid sequence of SEQ ID NO: 1 may take a modified form in which partial amino acids, or one or more amino acid residues of the sequence, have been modified, so long as the peptide exhibits cholesterol efflux from foam cells.

No limitations are imposed on the degree and the site of the modification (i.e., substitution, deletion, addition, or insertion), so long as a peptide having the modified amino acid sequence exhibits the same effect as peptides having the amino acid sequence of SEQ ID NO: 1; i.e., the peptide exhibits cholesterol efflux from foam cells. Examples of the mutant include peptides having about 100 amino acid residues, and the mutant preferably has about 6 to about 60 amino acid residues, more preferably about 20 to about 50 amino acid residues. An essential requirement is that the mutant have the six amino acid residues represented by SEQ ID NO: 4, and preferably the mutant has the 20 amino acid residues represented by SEQ ID NO: 5. Examples of the mutant include a peptide having the 30 amino acid residues represented by SEQ ID NO: 2, and a peptide having the 30 amino acid residues represented by SEQ ID NO: 3. The HDL-reactive peptide of the present invention is particularly preferably a peptide having the amino acid sequence of SEQ ID NO: 1.

Whether or not the foam-cell-reactive peptide has an ability to efflux cholesterol from foam cells may be confirmed in accordance with the procedure described below in Examples.

Hereinafter, the HDL-reactive peptide and the foam-cell-reactive peptide may collectively be referred to as "the present peptide."

The present peptide may be produced so as to have the mentioned amino acid sequence through a routine chemical synthesis method. The method encompasses a variety of peptide synthesis schemes on the basis of customary solid phase techniques and customary liquid phase techniques.

Specifically, the peptide synthesis methods include stepwise elongation and fragment condensation. In stepwise elongation, the peptide is produced through sequentially binding an amino acid residue in accordance with the amino acid sequence information of interest, whereby the chain is elongated. In fragment condensation, the peptide is produced through, in accordance with the amino acid sequence information of interest, synthesizing fragments having a plurality of amino acid residues and subsequently subjecting the fragments to coupling reaction with one another. The present peptide may be synthesized through either of these methods.

The condensation employed in the peptide synthesis described above may be performed through a routine method. Specific examples of the method include the azide method, the mixed acid anhydride method, the DCC method, the active ester method, the oxidation-reduction method, the DPPA (diphenylphosphorylazide) method, a modified DCC method which is a combination of the DCC method and an additive (e.g., 1-hydroxybenztriazole, N-hydroxysuccinamide, N-hydroxy-5-norbornene-2,3-dicarboxyimide), and the Woodward method. Solvents to be used in these methods can be suitably selected from among those which are well known to be employable in such a peptide condensation reaction. Examples of the solvents include dimethylformamide (DMF), dimethylsulfoxide (DMSO), hexaphosphoramide, dioxane, tetrahydrofuran (THF), ethyl acetate, and mixtures thereof.

In the peptide synthesis reaction, a carboxyl group which is contained in an amino acid or a peptide and which does not participate in the reaction may typically be protected through formation of an ester; e.g., a lower-alkyl ester such as a methyl ester, an ethyl ester, or a tert-butyl ester; a benzyl ester; a p-methoxybenzyl ester; a p-nitrobenzyl ester; or an aralkyl ester. When an amino acid residue has a functional group at its side chain, the functional group may be protected. For example, the hydroxyl group of Tyr may be protected with an acetyl group, a benzyl group, a benzyloxycarbonyl group, or a tert-butyl group. However, such a functional group may not necessarily be protected. In addition, the guanidino group of Arg may be protected with a suitable protecting group such as a nitro group, a tosyl group, a 2-methoxybenzenesulfonyl group, a methylene-2-sulfonyl group, a benzyloxycarbonyl group, an isobornyloxycarbonyl group, or an adamantyloxycarbonyl group.

Deprotection of the above-described protected amino acid or peptide or the finally obtained present peptide in a protected form may be performed through a routine method; e.g., a catalytic reduction, or a method employing liquid ammonia/sodium, hydrogen fluoride, hydrogen bromide, hydrogen chloride, trifluoroacetic acid, acetic acid, formic acid, or methanesulfonic acid.

In accordance with needs, the thus-obtained present peptide may be purified through a routine method. Examples of the method include ion exchange, partition chromatography, gel chromatography, affinity chromatography, high performance liquid chromatography (HPLC), and countercurrent distribution. These methods have been customarily used in the field of peptide chemistry.

Alternatively, the present peptide may be produced through a gene engineering technique which utilizes a DNA sequence encoding the present peptide.

The gene engineering technique may be performed through a routine procedure. For example, synthesis of a DNA fragment, production of a vector which enables expression of the DNA fragment, and expression of the vector in a host cell may be performed through procedures similar to those used in customary gene engineering techniques (see, for example, Molecular Cloning 2d. Ed., Cold Spring Harbor Lab. Press (1989); or Zoku-seikagaku Jikken Kouza "Idenshi Kenkyu-ho I, II, III," edited by The Japan Biochemical Society (1986)). For example, a DNA fragment encoding the present peptide is produced through a routine method in accordance with the amino acid sequence information on the HDL-binding peptide provided in the present invention (see, for example, Science, 224, 1431 (1984); Biochem. Biophys. Res. Comm., 130, 692 (1985); or Proc. Natl. Acad. Sci., USA., 80, 5990 (1983)).

More specifically, the DNA fragment may be chemically synthesized through a phosphoramidite method or a triester method. Examples of such a method include a method using a commercially available automated oligonucleotide synthesis device. A double-stranded DNA fragment is produced from the chemically synthesized single-stranded DNA fragment through synthesizing a DNA fragment complementary to the single-stranded DNA fragment and subjecting both of the fragments to an annealing procedure under suitable conditions, or through using a suitable primer and a DNA polymerase and adding a complementary DNA fragment to the single-stranded DNA fragment.

In accordance with needs, the amino acid sequence encoded by the DNA fragment may be modified. This can be done through a known method. Examples of the method include oligonucleotide directed site specific mutagenesis (Zoller, M., et al., Nucl. Acids Res., 10, 6487-6500 (1982)) and cassette mutagenesis (Well, J., et al., Gene, 34, 315-323 (1985)).

Production or expression of a desired peptide through use of the DNA fragment may be performed through a customary method known in the art (see, for example, Science, 224, 1431 (1984); Biochem. Biophys. Res. Comm., 130, 692 (1985); or Proc. Natl. Acad. Sci. USA., 80, 5990 (1983)).

A DNA fragment encoding the present peptide may be prepared by use of an existing DNA fragment capable of encoding apo B-100.

The thus-obtained peptide of interest may be isolated and purified through an isolation technique utilizing its physical or chemical characteristics (see, for example, "Biochemistry Data Book II," pp. 1175-1259, 1st edition, 1st printing, Jun.

23, 1980, published by Tokyo Kagaku Dozin Co., Ltd; Biochemistry, 25 (25), 8274-8277 (1986); or Eur. J. Biochem., 163, 313-321 (1987)).

As described above, the present peptide includes a peptide having a specific binding ability to HDL cholesterol and a peptide inducing cholesterol efflux from peripheral tissues, particularly from foam cells. Accordingly, utilizing these effects, the present peptide is used as a reagent for studies to explain the mechanism of lipid transcription and metabolism, arteriosclerosis occurrence mechanism in peripheral tissues, or the thrombus formation mechanism. In addition, for example, the present peptide may be used in production of a drug composition containing a peptide as an active ingredient. Since the drug composition contains, as an active ingredient, the present peptide exhibiting a specific binding ability to HDL cholesterol, the drug composition can be used, for example, to provide reactivity with HDL to TG-rich lipoproteins or abnormal lipoproteins (such as RLP) which are slowly metabolized and built up in blood, or to promote the reaction. Moreover, since the present peptide causes cholesterol efflux from peripheral tissue cells, the drug composition can be used for ameliorating lipid metabolism in the coronary artery, the aorta, the peripheral artery, etc. and for preventing or treating arteriosclerosis.

Thus, metabolism of such lipoproteins can be normalized or promoted, and development of arteriosclerosis can be prevented. Therefore, the drug composition can be used as a remedy for ameliorating lipid metabolism or as a remedy for preventing or treating arteriosclerosis.

The drug composition is administered such that the active ingredient is effectively delivered to target sites such as RLP, TG-rich lipoprotein, or the artery (particularly, the blood vessel). For example, the drug composition is administered via food, or the drug composition is processed such that the active ingredient is absorbed at the intestine to thereby prepare a drug preparation, and the preparation is administered perorally. Such a drug preparation may be produced through a routine method and administered in a customary manner. Optionally, the present peptide, the active ingredient of the drug composition, may be treated with lipid or other substances.

The drug composition may be combined with a drug delivery system (DDS) using a drug delivery substance which binds to the target RLP or TG-rich lipoprotein.

Examples of the drug delivery substance include antibodies (preferably polyclonal antibodies) for an apoprotein contained in a target lipoprotein, such as apo B-100. The present peptide which has been modified with such an antibody can achieve effective targeting by the target lipoprotein.

The drug composition contains a pharmacologically effective amount of the present peptide as an active ingredient, and the composition is prepared through a routine process together with one or more pharmacologically acceptable carriers, to thereby prepare the drug composition.

The present invention provides a DNA fragment having a nucleotide sequence encoding the present peptide. The DNA fragment is useful in production of the present peptide through a gene engineering technique as described above. In addition, the DNA fragment may be used in production of a drug composition containing a DNA fragment as an active ingredient. The resultant drug composition is used as a drug whose target is RLP, TG-rich lipoprotein, or the artery, and the drug composition is useful in the same use as that of the drug composition containing the present peptide as an active ingredient as described above.

The present peptide causes efflux of cholesterol and/or lipid such as TG from HDL. Therefore, the present peptide can be used, by reacting with HDL, for activation of reverse cholesterol transport or promotion of favorable HDL metabolism as described above. In order to use the present peptide, for example, a drug composition containing the present peptide or a DNA fragment thereof as an active ingredient may be produced, or the present peptide may be used to produce HDL having no cholesterol (hereinafter referred to as "Lipid free apo A-1") through efflux of cholesterol from HDL (see, for example, Curr. Opin. Lipidol., 7, 82-87, (1986)).

When the present peptide is used in the manner described above, the present peptide reacts with HDL, to thereby attain positive production of lipid free apo A-1 in blood. Thus, the present peptide can be used quite effectively in, among others, prevention—via HDL—of cholesterol deposit on tissues, or prevention of arteriosclerosis or restenosis of blood vessels, through forced efflux of cholesterol.

As described above, the present peptide has a direct effect of cholesterol efflux from foam cells in the artery. Therefore, even if the present peptide is applied to blood vessels which have already developed arteriosclerosis, the present peptide is quite useful in, for example, prevention of development of arteriosclerosis or treatment of arteriosclerosis, or prevention of restenosis of blood vessels via cholesterol efflux.

Use of the present peptide as a drug composition encompasses its use in vitro.

As described above, when the present peptide reacts with HDL, lipid free apo A-1 is produced, and the lipid free apo A-1 is useful for prevention or treatment of the above diseases or pathological conditions. Examples of the use of the present peptide in vitro include extracorporeal circulation using a column containing the present peptide as an effective component. No limitations are imposed on the mode of the extracorporeal circulation, so long as the mode enables the present peptide to effectively contact with test blood samples (HDL). For example, a carrier to which the present peptide is immobilized is preferably employed. In addition to a process using the carrier to which the present peptide is immobilized, extracorporeal circulation may be performed through the process described in Japanese Patent No. 2835923.

EXAMPLES

The present invention will next be described in more detail by way of examples, which should not be construed as limiting the invention thereto.

Example 1

(1) Peptide Synthesis

A peptide having an amino acid sequence of SEQ ID NO: 1 (B100FL) was chemically synthesized in accordance with a conventional method.

Specifically, the peptide was synthesized through the Fmoc method so as to attain the above sequence by use of Fmoc-NH-SAL resin (product of Watanabe Kagaku). The protected peptide-bearing resin was treated with a solvent mixture (TFA:phenol:thioanisole:1,4-butanedithiol:water=82.5:5:5:2.5:5) for three hours, to thereby remove the protecting groups.

The crude product was purified by reverse phase HPLC as described below, to thereby yield the target peptide.

<Reverse Phase HPLC>
Column: Cosmosil 5C18MS (10×250 mm; Nacalai Tesque)
Eluent: water/acetonitrile containing 0.1% TFA (linear gradient of acetonitrile; 2.5 mL/min.)
The thus-obtained target peptide was analyzed by mass spectrometry (Perseptive Biosystems; Voyager DE/matrix assisted laser desorption ionization-time of flight: MALDI-TOF/matrix: alpha-cyano-4-hydroxycinnamic acid) and amino acid analysis (hydrolysis in a constant boiling hydrochloric acid at 110° C. for 24 hours in a sealed tube (Hitachi L-8500 Amino Acid Analyzer)).

(2) Reactivity with anti-apo b-100 Monoclonal Antibody (JI-H: J. Clin. Ligand Assay, 19 (3), 177 (1999))
The reactivity was confirmed through ELISA in accordance with a conventional method by using a plate coated with the peptide obtained above (B100FL) (see Japanese Patent Application Laid-Open (kokai) No. 4-104798).
As a result, B100FL was found to have specific reactivity with JI-H (FIG. 1: the Y-axis and the X-axis represent absorbance (OD450) and immobilized peptide concentration (ng/mL), respectively).

(3) Reactivity with HDL
The peptide obtained in (1) above (B100FL, 0.1 mg) was added to affinity gel (25 μL) to which an anti-apo B-100 monoclonal antibody (JI-H) had been immobilized, whereby a B100FL-bound affinity gel was prepared. A control gel was prepared by treating gel with PBS (not containing B100FL) in a manner similar to the above.
Human plasma (1 mL) was added to affinity gel (2 mL) to which an anti-apo A-I monoclonal antibody had been immobilized, to thereby cause HDL to be specifically bound to the gel. The bound HDL was eluted with 3M sodium thiocyanate, and the buffer of the thus-obtained eluent was changed to PBS through use of a column for desalting, to thereby prepare an HDL sample.
The aforementioned anti-apo A-I monoclonal antibody immobilized affinity gel and anti-apo B-100 monoclonal antibody (JI-H) immobilized affinity gel were prepared in accordance with a conventional method (Japanese Patent Publication (kokoku) No. 7-104351).
The HDL sample (containing 20 μg of apo A-I) was reacted with the B100FL-bound affinity gel for 30 minutes at room temperature. Subsequently, the reaction mixture was left to stand for 15 minutes to thereby cause the gel to precipitate, to thereby remove the gel from the reaction mixture.
Fractions that did not bind to the gel (hereinafter referred to as "B100FL-unbound fractions") and the fractions that bound to the gel (hereinafter referred to as "B100FL-bound fractions") were separately subjected to the analysis described below in accordance with a conventional method.
Total cholesterol level: Total cholesterol level was determined with a reagent for measuring cholesterol level (L-TCII, Kyowa Medex Co., Ltd.) by means of an autoanalyzer (TBA20R; Toshiba).
Lipoprotein analysis: Lipoprotein was analyzed through HPLC of a lipoprotein analysis system (Lipopropax XL, eluent: TSK eluent LP-1, 1 mL/min., sample volume: 100 μL; Tosoh) by monitoring colors produced by cholesterol.
Protein concentration: Each protein concentration was determined by measuring absorbance (OD280); or through the Lowry method in which each sample (which had been delipidized with ethanol-ether) was subjected to color reaction.

Protein analysis: Protein was analyzed by SDS-gel electrophoresis. Specifically, each sample was subjected to delipidizing treatment and solubilized with 1% SDS, followed by treatment with a buffer (2% SDS/10% glycerol/0.005% BPB/20% 2-mercaptoethanol), to thereby prepare a sample for electrophoresis. The resultant sample was electrophoresed in a 4-20% gradient gel in accordance with a conventional method.

Figure 2:
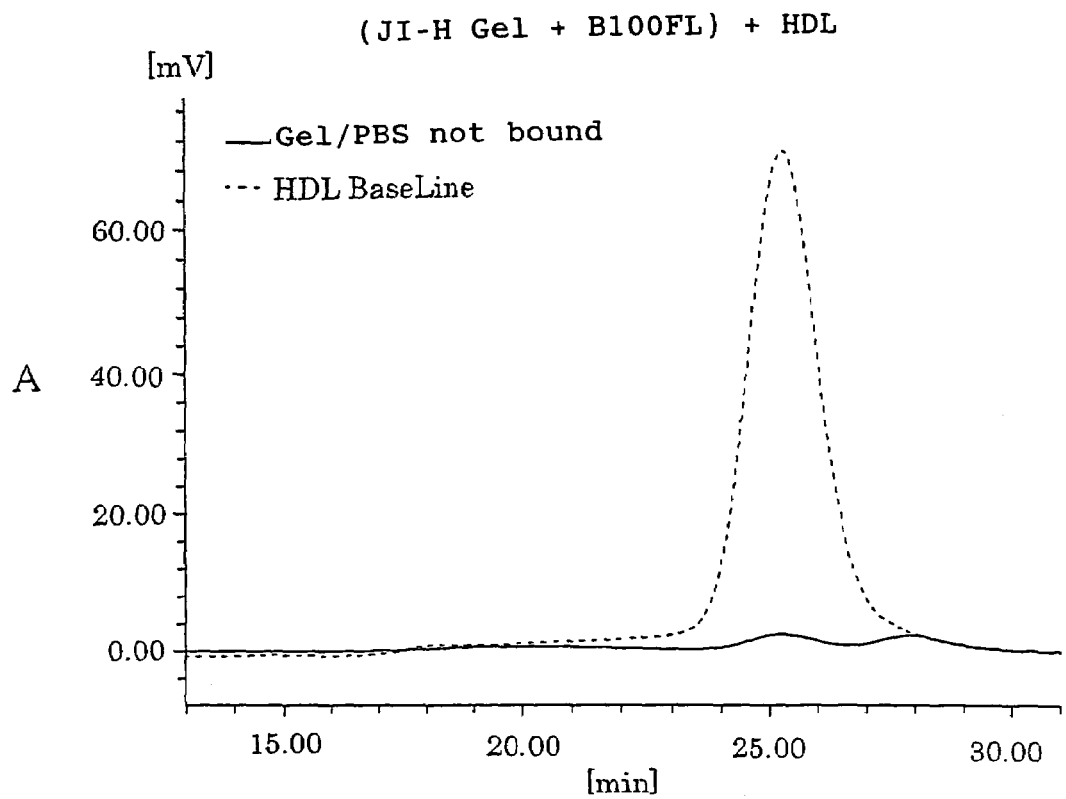
FIG. 2 shows the results of analysis (HPLC) of lipoproteins contained in a fraction that did not bind to the B100FL gel (A) and a fraction that did not bind to the control gel (B)
Figure 2:
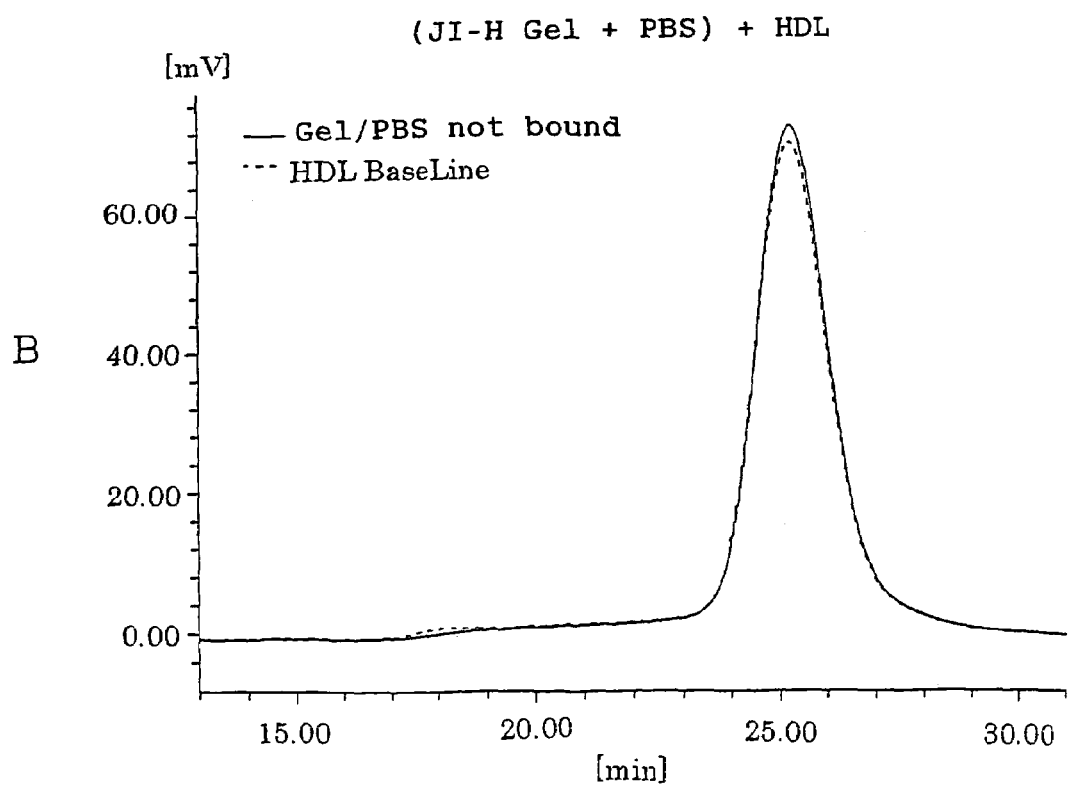

<Results>
FIG. 2 shows the results obtained by the analysis of lipoprotein contained in a fraction that did not bind to the B100FL gel (FIG. 2A) and a fraction that did not bind to the control gel (FIG. 2B). In FIG. 2, the solid lines show the results obtained by analysis in which each fraction was used as a sample; and the broken lines show the results obtained by analysis in which HDL was used as a sample (baseline).
Table 1 below shows the results obtained by each analysis of a fraction that did not bind to the B100FL gel ("B100FL" in Table 1) and a fraction that did not bind to the control gel ("PBS" in Table 1). Each analysis was performed with regard to total cholesterol level ("Cholesterol" in Table 1), HDL-cholesterol level ("HDL-C" in Table 1) obtained by lipoprotein analysis (FIG. 2), protein concentration determined by measuring absorbance ("O.D.280" in Table 1), and protein concentration measured through a color reaction ("Delipid Protein" in Table 1).

TABLE 1

|  | Cholesterol (mg/dl) | HDL-C (Area) | O.D. 280 | Delipid Protein (μg/mL) |
| --- | --- | --- | --- | --- |
| B100FL | 0.25 | 243.2 | 0.116 | 231.0 |
| PBS | 3.60 | 5,811.3 | 0.143 | 215.8 |

Figure 3:
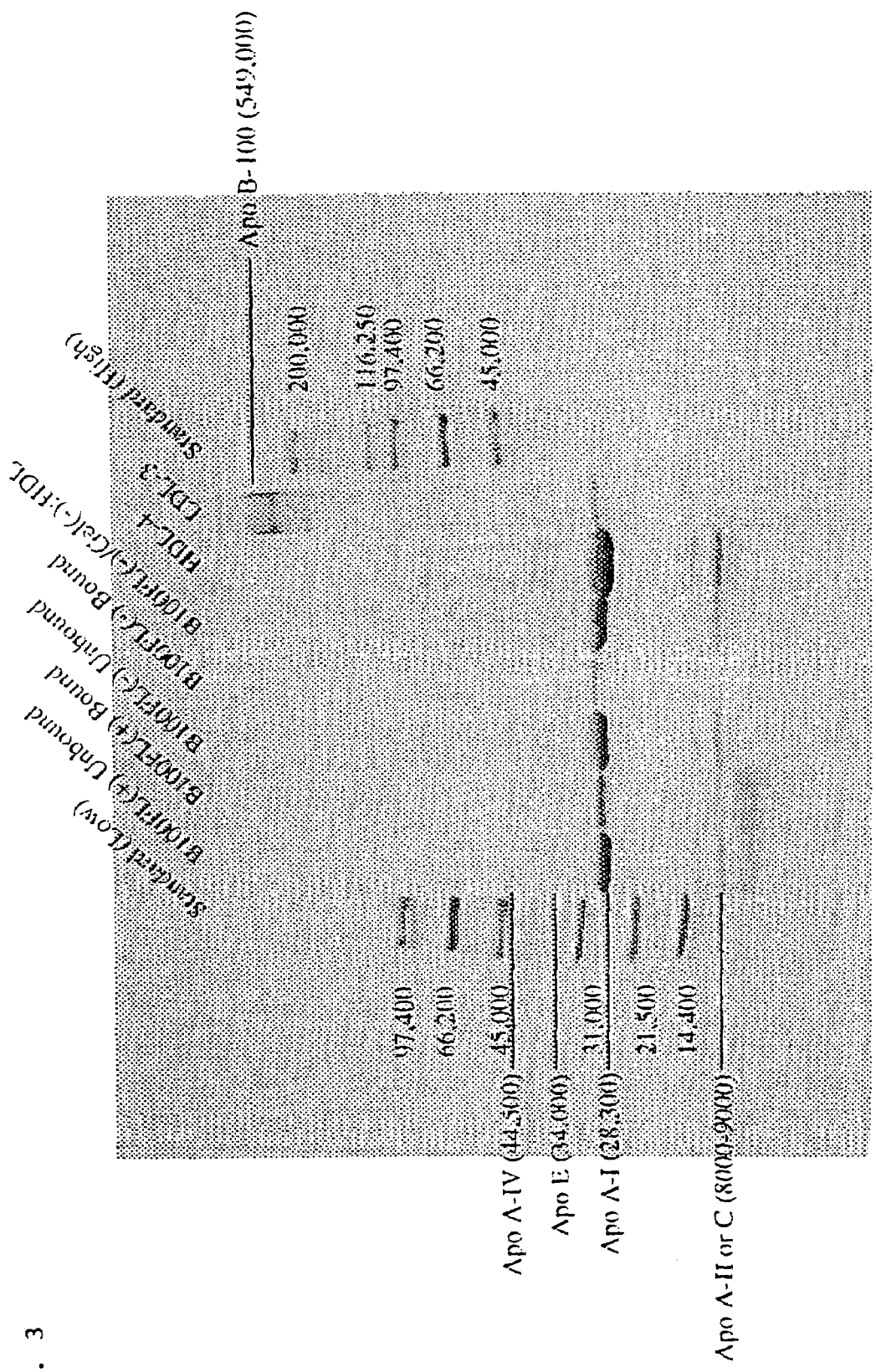
FIG. 3 shows the results of analysis (SDS gel electrophoresis) of proteins contained in a fraction that did not bind to the B100FL gel and a fraction that did bind to the B100FL gel.

As is clear from Table 1, the total cholesterol level of the HDL sample treated with B100FL-bound gel is 0.25 mg/dl, which is about 1/15 that of the HDL sample treated with the control gel. Moreover, FIG. 2 (lipoprotein analysis), includes a peak attributed to cholesterol (HDL-C) in the HDL sample that had been treated with the control gel, but does not include a peak in the HDL sample that had been treated with B100FL-bound gel.
The protein concentration was determined by measuring absorbance and through a color reaction. The protein concentration of the HDL sample that had been treated with B100FL-bound gel was found to be almost same as that of the HDL sample that had been treated with the control gel (Table 1).
Protein analysis was performed through SDS-gel electrophoresis. The results are shown in FIG. 3.
In FIG. 3, each lane represents the following sample.
Standard (Low): Low molecular weight standard
B100FL (+) Unbound: B100FL-unbound fraction
B100FL (+) Bound: B100FL-bound fraction
B100FL (−) Unbound: Control-gel-unbound fraction
B100FL (−) Bound: Control-gel-bound fraction
B100FL (−)/Gel (−): HDL: HDL that had not been treated with gel
HDL-4: HDL-fraction 4 that had not been treated with gel
LDL-3: LDL-fraction 3 that had not been treated with gel
Standard (High): High molecular weight standard
In FIG. 3, not only in the untreated HDL sample but also in the sample that had been treated with B100FL-bound gel, a band which represents A-1 (a main apoprotein of HDL) is present as a main band in the vicinity of the position of molecular weight 28,000. Furthermore, bands which represent HDL-structuring proteins other than A-I (apo C, apo A-II, apo E, apo A-IV, etc.) are also present, and no difference is found in the structural ratio of these proteins.

Accordingly, in a reaction solution obtained by reacting HDL with B100FL, only proteins (for example, apo A-I of HDL) are present, and cholesterol and cholesterol ester are substantially absent. The above results indicate that B100FL has an interaction with cholesterol and cholesterol ester of HDL, and has an effect of effluxing cholesterol and cholesterol ester from apoprotein particles of HDL.

Example 2

Peptide Synthesis

Each peptide having an amino acid sequence shown in Table 2 was synthesized in a manner similar to that described in Example 1.

minutes at 10,000 rpm. The cholesterol level of the supernatant was measured by means of the autoanalyzer described above.

Each test peptide was dissolved in DMSO (5 mg/mL), and the thus-formed solution was diluted with DMEM so as to attain a concentration of 1 mg/mL. Subsequently, the resultant solution was diluted 10-fold or 100-fold with DMEM, to thereby prepare a test sample. Moreover, in order to prepare a control sample, only DMSO was diluted with DMEM so as to attain a final concentration of 0.4, 0.04, or 0.004%; and in order to prepare a positive control sample, delipid HDL was diluted with DMEM so as to attain a concentration of 2.5, 5.0, or 10 µg/mL.

Figure 4:
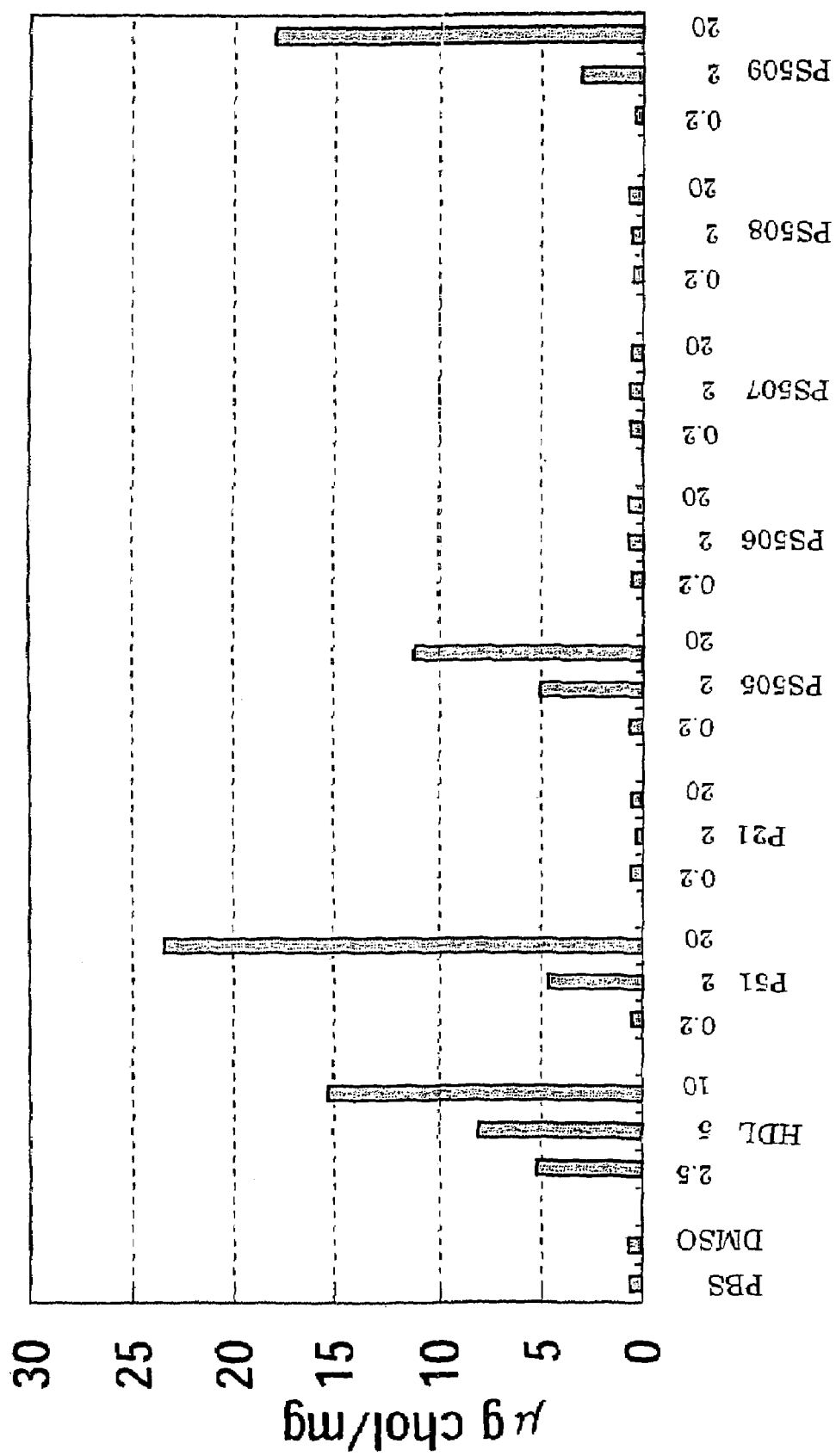
FIG. 4 shows the effect of the present peptide in cholesterol efflux from RAW264 cells.

The results are shown in FIG. 4.

Three peptides (P51 (B-100FL, SEQ ID NO: 1), PS505 (SEQ ID NO: 2), and PS509 (SEQ ID NO: 3)) were found to exhibit strong cholesterol efflux effect from RAW264

TABLE 2

| Name | M.W. | Amino acid sequence | Apo B-100 position |
|---|---|---|---|
| P51 (B-100FL) | 5,931 | LLDQLGTTIS FERINDVLEH VKHFVINLIG DFEVAEKINA FRAKVHEL IE R | (2,297–2,347) |
| P21 | 2,514 | DFEVAEKINA FRAKVHEL IE R | (2,327–2,347) |
| PS505 (SEQ ID NO: 2) | 3,434 | LLDQLGTTIS FERINDVLEH VKHFVINLIG | (2,297–2,326) |
| PS506 | 2,824 | LLDQLGTTIS FERINDVLEH VKHF | (2,297–2,320) |
| PS507 | 1,834 | LLDQLGTTIS FERIND | (2,297–2,312) |
| PS508 | 1,952 | EKINA FRAKVHEL IE R | (2,332–2,347) |
| PS509 (SEQ ID NO: 3) | 3,509 | FERINDVLEH VKHFVINLIG DFEVAEKINA | (2,307–2,336) |

Example 3

Cholesterol Efflux Test

The aforementioned peptides were examined with regard to cholesterol efflux effect from RAW264 cells (a model of atherosclerosis).

Specifically, RAW264 cells (mouse monocytic leukemia cell strain) were added to DMEM medium that had been supplemented with 10% FBS, to thereby prepare a specimen having a concentration of 4×10⁵ cells/mL. An aliquot of the specimen (1 mL) was added to each well of a 12-well plate, followed by culture for two days in a $CO_2$ incubator (37° C.). The medium in each well was removed, and the cells in the well were washed once with 1 mL of DMEM containing 0.2% BSA and 20 mM glutamine (hereinafter referred to as "DMEM"). Subsequently, a solution of acetylated LDL in DMEM (40 µg/mL, 1 mL) was added to each well, followed by culture for 24 hours in a $CO_2$ incubator (37° C.), whereby acetylated LDL entered into the cells. The cells were washed twice with PBS supplemented with 0.2% BSA. Thereafter, a solution of dibutyl cAMP in DMEM (0.3 mM, 1 mL) was added to each well, followed by incubation for 2 hours in a $CO_2$ incubator (37° C.).

The test peptide (20 µL) was added to each well so as to attain a final concentration of 20, 2.0, or 0.2 µg/mL, followed by culture for 24 hours in a $CO_2$ incubator (37° C.).

After 24 hours, the supernatant of each well was collected in a microtube, and the microtube was centrifuged for five cells (foam with acetylated LDL) depending on the concentrations of the employed peptides. However, four peptides (P21, PS506, PS507, and PS508) not containing a sequence composed of six amino acids (corresponding to the 2,321-2,326th amino acids of B-100) were found not to exhibit the effect.

Conceivably, a peptide containing a sequence of six amino acids (2,321-2,326th amino acids of B-100) (SEQ ID NO: 4) and a peptide containing a sequence of 20 amino acids (2,307-2,326th amino acids of B-100) (SEQ ID NO: 5) exhibit a cholesterol efflux effect, and have an anti-arteriosclerosis effect.

Example 4

Effect Test by Use of an Arteriosclerosis Model

Cholesterol (Wako Pure Chemical Industries, Ltd.) and corn oil (Corn Germ Oil 100; Ajinomoto Co., Inc.) were incorporated into a commercially available feed (product of Natural Pet Foods, "Chicks and nestlings (Quail)") so as to attain final concentrations of 2% and 15%, respectively, to thereby prepare a high-cholesterol feed.

Healthy quails were bred while being allowed to freely intake the high-cholesterol feed for eight weeks. From five weeks after the beginning of breeding, a solution of the test peptide (B-100FL) in saline (1.0 mg/mL) was administered to the brachial (wing) vein (200 µL; 200 µg/body) twice a week at the interval of two through three days. In a manner similar to that described above, only saline was administered to the quails of a control group.

After the quails had been bred for eight weeks, the head of each quail was cut for exsanguination, and an aorta sample was obtained. The aorta sample was immediately fixed in a fixing solution (10% formalin) for three days. Subsequently, a tissue specimen (a frozen section having a thickness of 4 μm) of the aortic arch (where arteriosclerosis foci are most likely to occur) was prepared. The tissue specimen was subjected to hematoxylin-and-eosin staining (routine staining), and to oil-red staining (fat staining), followed by examination under a microscope.

In the tissue specimens of the control group, the following were observed: considerable thickening of the vessel internal tunica, accumulation of a large amount of lipid in the thickening portions of the internal tunica, infiltration of lipids into numerous portions (not only the internal tunica but the middle tunica), and tissues including lipids and smooth muscle cells existing among the elastic fibers.

In the tissue specimen of the group to which a test peptide had been administered, a small amount of lipid accumulation was observed in the internal tunica. However, the accumulated lipid size and amount were small, and no morphological disorder of the vessel internal tunica was observed. In addition, thickening of the internal tunica and lipid infiltration into the middle tunica were found to be absent.

Figure 5:
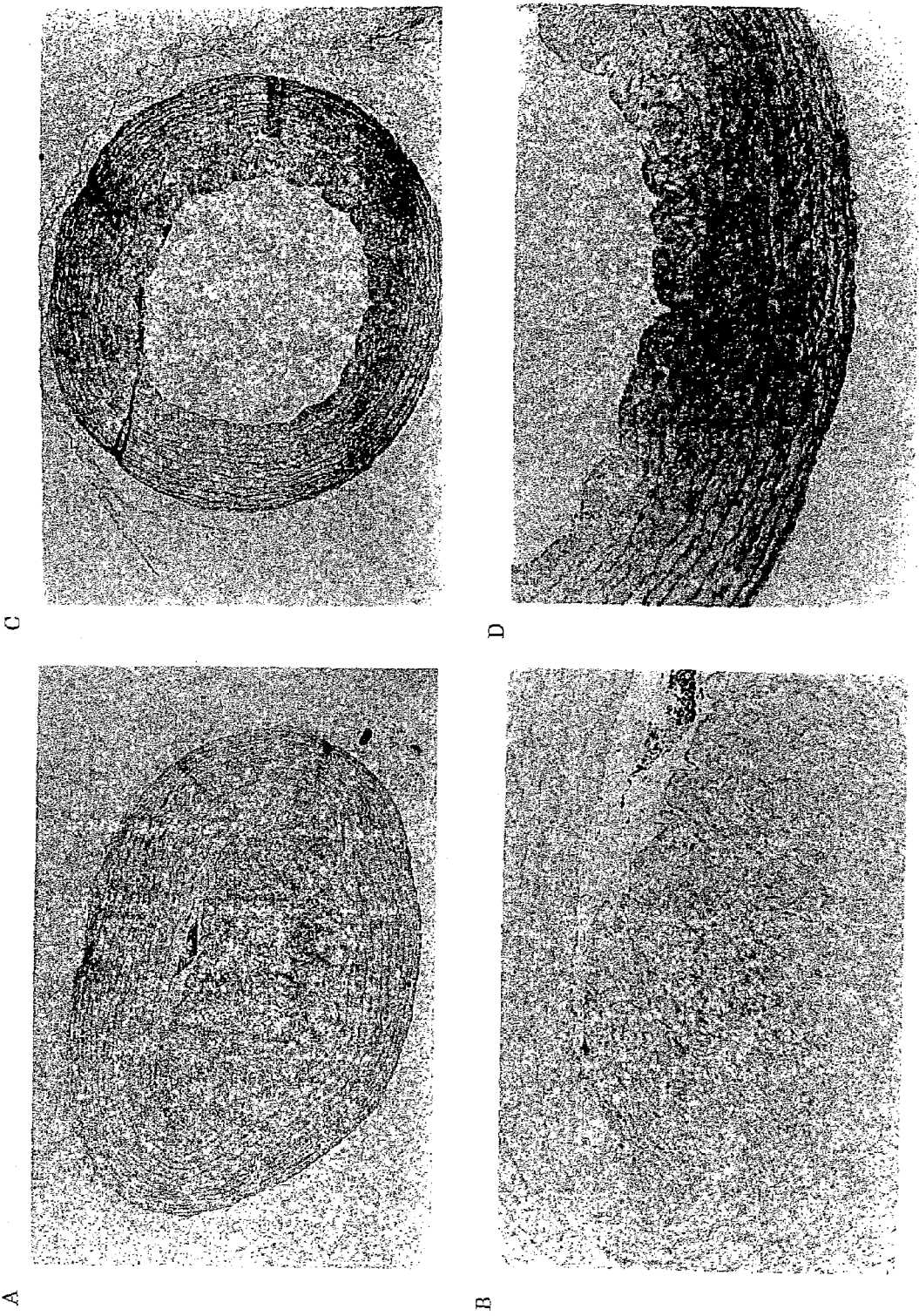
FIG. 5 shows effect of the present peptide on the blood vessel tissues of quail arteriosclerosis model (A (×16) and B (×40): the control groups, and C (×16) and D (×40): the groups to which the present peptide had been administered).

FIG. 5 shows typical images of the tissue specimens. In FIG. 5, A (×16) and B (×40) represent images of the tissue specimens of the control group, and C (×16) and D (×40) represent images of the tissue specimens of the test group.

As is clear from the above description, the peptides of the present invention inhibit occurrence of arteriosclerosis foci in an early stage by preventing infiltration of lipids into the vessel; and arrest development of such foci by efflux of infiltrated lipids from the vessel.

Example 5

In a manner similar to that described in Example 1 (3), reactivity of PS509 (synthesized in Example 2) with HDL was examined (as a test peptide, B-100FL or PS509 was employed, and the total cholesterol level of the applied HDL sample was 12.7 mg/dl).

When HDL was treated with B-100FL, the total cholesterol level was reduced by about 72 percentage points, whereas when HDL was treated with PS509, the total cholesterol level was reduced by about 48 percentage points.

INDUSTRIAL APPLICABILITY

The present invention provides a peptide having a novel amino acid sequence having a HDL-cholesterol-specific binding ability. Also, the present invention provides a peptide which causes efflux of cholesterol from peripheral tissue. These peptides are useful as a drug for a variety of diseases caused by, for example, arteriosclerosis, lipid metabolic errors, and peripheral tissue cholesterol build-up.

The invention claimed is:

1. An isolated high density lipoprotein reactive peptide (a) or (b):
   (a) an isolated peptide consisting of the amino acid sequence SEQ ID NO: 1; or
   (b) an isolated peptide comprising either the amino acid sequence of SEQ ID NO: 2 or the amino acid sequence of SEQ ID NO: 3, wherein the isolated peptide is at most 51 amino acids in length; and wherein the isolated high density lipoprotein reactive peptide (a) or (b) binds to high density lipoprotein cholesterol.

2. The isolated high density lipoprotein reactive peptide according to claim 1, wherein the isolated high density lipoprotein consists of (a) the amino acid sequence SEQ ID NO: 1.

3. The isolated high density lipoprotein reactive peptide of claim 1 which is (b) an isolated peptide comprising the amino acid sequence of SEQ ID NO: 2, wherein the isolated peptide is at most 51 amino acids.

4. The isolated high density lipoprotein reactive peptide of claim 1 which is (b) an isolated peptide comprising the amino acid sequence of SEQ ID NO: 3, wherein the isolated peptide is at most 51 amino acids.

5. A composition comprising, as an active ingredient, the isolated high density lipoprotein reactive peptide of claim 1 and a pharmacologically acceptable carrier.

6. A composition comprising, as an active ingredient, the isolated high density lipoprotein reactive peptide of claim 2 and a pharmacologically acceptable carrier.

7. A method of treating arteriosclerosis in a subject in need thereof comprising administering the composition of claim 5 to the subject in an amount sufficient to treat the arteriosclerosis.

8. A method of treating arteriosclerosis in a subject in need thereof comprising administering the composition of claim 6 to the subject in an amount sufficient to treat the arteriosclerosis.

9. An isolated foam cell reactive peptide (a) or (b):
   (a) an isolated peptide consisting of the amino acid sequence SEQ ID NO: 1; or
   (b) an isolated peptide comprising the amino acid sequence of SEQ ID NO: 2 or the amino acid sequence of SEQ ID NO: 3, wherein the isolated peptide is at most 51 amino acids in length; and wherein the isolated foam cell reactive peptide (a) or (b) induces cholesterol efflux from foam cells.

10. The isolated foam cell reactive peptide according to claim 9, which consists of (a) the amino acid sequence SEQ ID NO: 1.

11. The isolated foam cell reactive peptide according to claim 9, which binds to high density lipoprotein cholesterol.

12. The isolated foam cell reactive peptide of claim 9, which is (b) an isolated peptide comprising the amino acid sequence of SEQ ID NO: 2, wherein the isolated peptide is at most 51 amino acids in length.

13. The isolated foam cell reactive peptide of claim 9, which is (b) an isolated peptide comprising the amino acid sequence of SEQ ID NO: 3, wherein the isolated peptide is at most 51 amino acids in length.

14. A composition comprising, as an active ingredient, the isolated foam cell reactive peptide of claim 9 and a pharmacologically acceptable carrier.

15. A composition comprising, as an active ingredient, the isolated foam cell reactive peptide of claim 5 and a pharmacologically acceptable carrier.

16. A method of treating arteriosclerosis in a subject in need thereof comprising administering the composition of claim 14 to the subject in an amount sufficient to treat the arteriosclerosis.

17. A method of treating arteriosclerosis in a subject in need thereof comprising administering the composition of claim 15 to the subject in an amount sufficient to treat the arteriosclerosis.

* * * * *

UNITED STATES PATENT AND TRADEMARK OFFICE
CERTIFICATE OF CORRECTION

PATENT NO. : 7,241,861 B2  
APPLICATION NO. : 10/476872  
DATED : July 10, 2007  
INVENTOR(S) : Niimi Manabu et al.

It is certified that error appears in the above-identified patent and that said Letters Patent is hereby corrected as shown below:

Col. 18, Claim 15, line 2, "isolated foam cell reactive peptide of claim 5 and a" should read -- isolated foam cell reactive peptide of claim 10 and a --.

Signed and Sealed this

Twenty Second Day of April, 2008

JON W. DUDAS  
*Director of the United States Patent and Trademark Office*

SEQUENCE LISTING

<160> NUMBER OF SEQ ID NOS: 5

<210> SEQ ID NO 1
<211> LENGTH: 51
<212> TYPE: PRT
<213> ORGANISM: Artificial Sequence
<220> FEATURE:
<223> OTHER INFORMATION: synthetic peptide

<400> SEQUENCE: 1

Leu Leu Asp Gln Leu Gly Thr Thr Ile Ser Phe Glu Arg Ile Asn Asp
1               5                   10                  15

Val Leu Glu His Val Lys His Phe Val Ile Asn Leu Ile Gly Asp Phe
            20                  25                  30

Glu Val Ala Glu Lys Ile Asn Ala Phe Arg Ala Lys Val His Glu Leu
        35                  40                  45

Ile Glu Arg
    50

<210> SEQ ID NO 2
<211> LENGTH: 30
<212> TYPE: PRT
<213> ORGANISM: Artificial Sequence
<220> FEATURE:
<223> OTHER INFORMATION: synthetic peptide

<400> SEQUENCE: 2

Leu Leu Asp Gln Leu Gly Thr Thr Ile Ser Phe Glu Arg Ile Asn Asp
1               5                   10                  15

Val Leu Glu His Val Lys His Phe Val Ile Asn Leu Ile Gly
            20                  25                  30

```
<210> SEQ ID NO 3
<211> LENGTH: 30
<212> TYPE: PRT
<213> ORGANISM: Artificial Sequence
<220> FEATURE:
<223> OTHER INFORMATION: synthetic peptide

<400> SEQUENCE: 3

Phe Glu Arg Ile Asn Asp Val Leu Glu His Val Lys His Phe Val Ile
1               5                   10                  15

Asn Leu Ile Gly Asp Phe Glu Val Ala Glu Lys Ile Asn Ala
            20                  25                  30

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Val Ile Asn Leu Ile Gly
1               5

<210> SEQ ID NO 5
<211> LENGTH: 20
<212> TYPE: PRT
<213> ORGANISM: Artificial Sequence
<220> FEATURE:
<223> OTHER INFORMATION: synthetic peptide

<400> SEQUENCE: 5

Phe Glu Arg Ile Asn Asp Val Leu Glu His Val Lys His Phe Val Ile
1               5                   10                  15

Asn Leu Ile Gly
            20
```